United States Patent
Ge et al.

(10) Patent No.: US 11,965,945 B2
(45) Date of Patent: Apr. 23, 2024

(54) MAGNETIC RESONANCE SYSTEM AND SHIMMING METHOD AND IMAGING METHOD THEREOF

(71) Applicant: GE Precision Healthcare LLC, Wauwatosa, WI (US)

(72) Inventors: Yaan Ge, Beijing (CN); Liyuan Jin, Beijing (CN); Qingyu Dai, Beijing (CN); Kun Wang, Beijing (CN); Qilin Lu, Beijing (CN)

(73) Assignee: GE Precision Healthcare LLC, Wauwatosa, WI (US)

( * ) Notice: Subject to any disclaimer, the term of this patent is extended or adjusted under 35 U.S.C. 154(b) by 0 days.

(21) Appl. No.: 17/893,970

(22) Filed: Aug. 23, 2022

(65) Prior Publication Data

US 2023/0066519 A1 Mar. 2, 2023

(30) Foreign Application Priority Data

Aug. 31, 2021 (CN) .......................... 202111016148.0

(51) Int. Cl.
 *G01V 3/00* (2006.01)
 *A61B 5/00* (2006.01)
 *A61B 5/055* (2006.01)
 *G01R 33/54* (2006.01)

(52) U.S. Cl.
 CPC .......... *G01R 33/543* (2013.01); *A61B 5/0037* (2013.01); *A61B 5/055* (2013.01); *A61B 5/7264* (2013.01)

(58) Field of Classification Search
 CPC ............. G01R 33/3415; G01R 33/543; G01R 33/5659; G01R 33/36; A61B 5/055
 USPC ......................................................... 324/307
 See application file for complete search history.

(56) References Cited

U.S. PATENT DOCUMENTS 10,145,929 B2 * 12/2018 Stemmer .............. G01R 33/243
2019/0346519 A1 * 11/2019 Nitta .................. G01R 33/3875

FOREIGN PATENT DOCUMENTS

| CN | 1263601 A | * | 8/2000 | ........ G01R 33/3415 |
| CN | 110276721 A | * | 9/2019 | |
| EP | 3081955 A1 | * | 10/2016 | ............. A61B 5/055 |
| WO | WO-2018135812 A1 | * | 7/2018 | ............... A61B 5/00 |

OTHER PUBLICATIONS

Islam et al., "Dynamic per slice shimming for simultaneous brain and spinal cord fMRI", Magn Reson Med. Feb. 2019;81(2):825-838, 24 pages.
Morrell et al., "Dynamic shimming for multi-slice magnetic resonance imaging", Magn Reson Med. Sep. 1997;38 (3):477-83, 7 pages.

* cited by examiner

Primary Examiner — Walter L Lindsay, Jr.
Assistant Examiner — Frederick Wenderoth

(57) ABSTRACT

Embodiments of the present application provide a magnetic resonance system and a shimming method and an imaging method thereof. The shimming method comprises: performing a scout scan on a subject to be examined, and obtaining phase data of a plurality of slice positions; determining three-dimensional space static magnetic field information according to the phase data of the plurality of slice positions; and determining a shimming value of a slice in a region of interest according to the three-dimensional space static magnetic field information.

17 Claims, 9 Drawing Sheets

MAGNETIC RESONANCE SYSTEM AND SHIMMING METHOD AND IMAGING METHOD THEREOF

CROSS REFERENCE

The present application claims priority and benefit of Chinese Patent Application No. 202111016148.0 filed on Aug. 31, 2021, which is incorporated herein by reference in its entirety.

TECHNICAL FIELD

Embodiments of the present application relate to the technical field of medical devices, and relate in particular to a magnetic resonance system and a shimming method and an imaging method thereof.

BACKGROUND

Magnetic resonance imaging (MRI) systems have been widely applied in the field of medical diagnosis. Magnetic resonance systems usually have a main magnet, a gradient radio-frequency amplifier, a gradient coil, a transmitting chain module, a transmitting/receiving coil, a receiving chain module, etc. MRI utilizes the main magnet to generate a static magnetic field B0. When a subject to be examined is located in the static magnetic field B0, nuclei associated with hydrogen nuclei in a tissue of the subject to be examined spin and become polarized, causing the tissue to be examined to produce a longitudinal magnetization vector macroscopically. After a radio-frequency field B1 intersecting the direction of the static magnetic field B0 is applied, the rotation direction of the protons changes, causing the tissue to be examined to produce a transverse magnetization vector macroscopically. After the radio-frequency field B1 is removed, the transverse magnetization vector decays in a spiral manner until it returns to zero. A free induction decay signal is generated during the decay process. The free induction decay signal can be acquired as a magnetic resonance signal, and an image of the tissue part to be examined can be reconstructed based on the acquired signal.

In the magnetic resonance imaging systems, the uniformity of the static magnetic field is a key factor in the quality of the magnetic resonance image. Non-uniformity of the static magnetic field will lead to magnetic susceptibility artifacts, poor fat saturation effects, image distortion, and even artifacts, etc. Therefore, shimming measures are usually adopted to improve the uniformity of the magnetic field within a specific range.

SUMMARY

At present, a static magnetic field B0 can be compensated using a magnetic field generated by an electromagnetic coil, and parameters of the compensating magnetic field can be obtained by calculating a shimming value, so as to achieve uniformity of the magnetic field. Commonly used methods for calculating the shimming value include calculating the shimming value by using a central slice in a pre-scan process. However, the performance of this method is limited in terms of fat saturation. In addition, the shimming method requires a long time, thus making the pre-scan process longer.

In view of at least one of the above technical problems, embodiments of the present application provide a magnetic resonance system and a shimming method and an imaging method thereof.

According to an aspect of the embodiments of the present application, provided is a shimming method of a magnetic resonance system. The method includes performing a scout scan on a subject to be examined, and obtaining phase data of a plurality of slice positions. The method also includes determining three-dimensional space static magnetic field information according to the phase data of the plurality of slice positions; and determining a shimming value of a slice in a region of interest according to the three-dimensional space static magnetic field information.

According to an aspect of the embodiments of the present application, provided is an imaging method of a magnetic resonance system. The imaging method includes the shimming method described in the previous aspect; determining a diagnostic scan parameter according to the shimming value; and performing a diagnostic scan according to the diagnostic scan parameter, and obtaining a magnetic resonance diagnostic image in the region of interest.

According to an aspect of the embodiments of the present application, provided is a magnetic resonance system. The system includes a scanning unit; a controller, configured to control the scanning unit to perform a scout scan to obtain phase data of a plurality of slice positions; and a processor configured to determine three-dimensional space static magnetic field information according to the phase data of the plurality of slice positions. The processor is further configured to determine a shimming value of a slice in a region of interest according to the three-dimensional space static magnetic field information.

One of beneficial effects of the embodiments of the present application is that the shimming value of each slice in the region of interest is determined by using the phase data obtained during the scout scan process, thereby making it possible to reduce the pre-scanning time and more accurately correct non-uniformity of the B0 field, so as to provide better performance in terms of fat saturation in MRI.

With reference to the following description and accompanying drawings, specific implementations of the embodiments of the present application are disclosed in detail, and manners in which the principle of the embodiments of the present application is employed are illustrated. It should be understood that the implementations of the present application are not thereby limited in scope. Within the spirit and scope of the appended claims, the implementations of the present application comprise various changes, modifications, and equivalents.

BRIEF DESCRIPTION OF THE DRAWINGS

The accompanying drawings are included to provide further understanding of embodiments of the present application, constitute a part of the specification, and are used to illustrate implementations of the present application and set forth the principles of the present application together with textual description. Obviously, the accompanying drawings in the following description are merely some embodiments of the present application, and a person of ordinary skill in the art could obtain other implementations according to the accompanying drawings without the exercise of inventive effort. In the accompanying drawings.

DETAILED DESCRIPTION

Figure 1:
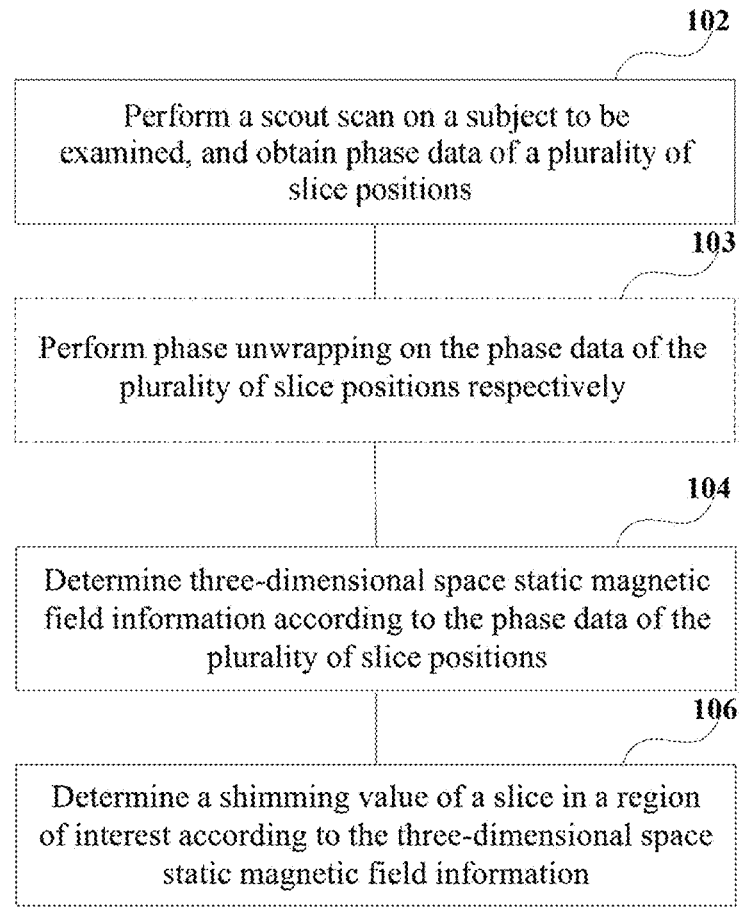
FIG. 1 is a schematic diagram of a shimming method of a magnetic resonance system according to an embodiment of the present application.

The foregoing and other features of the embodiments of the present application will become apparent from the following description with reference to the accompanying drawings. In the description and the accompanying drawings, specific implementations of the present application are specifically disclosed, and part of the implementations in which the principles of the embodiments of the present application may be employed are indicated. It should be understood that the present application is not limited to the described implementations. On the contrary, the embodiments of the present application include all modifications, variations, and equivalents falling within the scope of the appended claims.

In the embodiments of the present application, the terms "first," "second," etc. are used to distinguish different elements, but do not represent a spatial arrangement or temporal order etc. of these elements, and these elements should not be limited by these terms. The term "and/or" includes any one of and all combinations of one or more associated listed terms. The terms "comprise," "include," "have," etc. refer to the presence of described features, elements, components, or assemblies, but do not exclude the presence or addition of one or more other features, elements, components, or assemblies.

In the embodiments of the present application, the singular forms "a," "the," etc. include plural forms, and should be broadly construed as "a type of" or "a class of" rather than limited to the meaning of "one." Furthermore, the term "said" should be construed as including both the singular and plural forms, unless otherwise specified in the context. In addition, the term "according to" should be construed as "at least in part according to . . . ," and the term "based on" should be construed as "at least in part based on . . . ," unless otherwise specified in the context.

The features described and/or illustrated for one implementation may be used in one or more other implementations in the same or similar manner, combined with features in other implementations, or replace features in other implementations. The term "include/comprise" when used herein refers to the presence of features, integrated components, steps, or assemblies, but does not preclude the presence or addition of one or more other features, integrated components, steps, or assemblies.

In MRI, magnetic resonance scanning of a subject may include a pre-scan, a scout scan (three-plane scan), and a formal scan (diagnostic scan). During the pre-scan, pre-setting of the system may be completed. For example, frequency adjustment may be performed to determine the Larmor frequency of proton resonance or (the center frequency of this magnetic resonance examination) for the present scan on the basis of the feedback of magnetic resonance signals at different frequencies. Radio-frequency transmission intensity adjustment may be performed to determine the radio-frequency transmission power for the present scan on the basis of the feedback of magnetic resonance signals at different radio-frequency transmission intensities. One or more scanning sequences may be performed during the scout scan and the formal scan. Wherein, during the scout scan, scout images of three planes of the subject, such as at least one of a coronal (Cor) scout image, a sagittal (Sag) scout image, and an axial (Axial) scout image, can be obtained, and scan parameters of the formal scan, such as a region of interest (field of view, FOV) of the formal scan can be determined on the basis of the scout image. Medical images obtained from the formal scan can be used for clinical diagnosis.

In methods from the prior art, a pre-scan image can be obtained based on pre-scanning the subject, and based on the pre-scan image, uniformity analysis and adjustment of a static magnetic field B0 can be performed to implement shimming settings. For example, a shimming value can be calculated using a central slice (in the following description, "slice" and "layer" are interchangeable) image, but this method has limited performance in terms of fat saturation, and in addition, this shimming method takes a long time, thus making the pre-scan process longer.

In the present application, a shimming value of each slice in a region of interest is determined by using a phase image obtained during a scout scan process, thereby reducing pre-scanning time and more accurately correcting non-uniformity of a B0 field to provide better performance in terms of fat saturation in MRI. In addition, the method of performing dynamic shimming during the scout scan process is simple to implement and will not affect a scanning sequence.

The embodiments of the present application are specifically described below.

Embodiments of First Aspect

An embodiment of the present application provides a shimming method of a magnetic resonance system. FIG. 1 is a schematic diagram of the magnetic resonance shimming method according to this embodiment of the present application. As shown in FIG. 1, the method includes:

102, performing a scout scan on a subject to be examined, and obtaining phase data of a plurality of slice positions;
 104, determining three-dimensional space static magnetic field information according to the phase data of the plurality of slice positions; and
 106, determining a shimming value of a slice in a region of interest according to the three-dimensional space static magnetic field information.

In some embodiments, in 102, a scanning unit of a magnetic resonance system may execute a preset scanning sequence to perform the scout scan. For example, a variety of scanning sequences may be preset in the magnetic resonance system, and during the scout scan, a preset scanning sequence may be selected according to requirements. For example, the scanning sequence includes: a spin echo sequence, a gradient echo sequence, an inversion recovery sequence, etc. The spin echo sequence may include a fast spin echo (FSE) sequence, and the gradient echo sequence includes a fast gradient echo sequence (FGRE), etc., and the embodiments of the present application are not limited thereto.

In some embodiments, in 102, the scout scan of the aforementioned scanning sequence may be performed at the plurality of slice positions, and the positions and number of the plurality of slices may be set as required, and the embodiments of the present application are not limited thereto. For example, the number of slices may be set to 3, 5, 7, 9, etc., and there may also be a slice on which the scanning sequence is not executed between adjacent slices in the plurality of slices.

In some embodiments, the three-dimensional space static magnetic field information may also be referred to as a 3D B0 field map or a 3D B0 volume, which is used to reflect spatial distribution conditions of the static magnetic field. Since the magnitude of the applied B0 will affect the deflection angular velocity of a longitudinal magnetization vector of protons, and further, the magnitude of the static magnetic field has a certain functional relationship with a change of the phase of an echo signal with time, the three-dimensional space static magnetic field information may be obtained by calculating a difference between echo signals (a phase difference of a complex signal) acquired at different echo times. For example, for each of the plurality of slice positions, a plurality of echo signals are obtained at a plurality of echo times, and a plurality of scout images are generated according to the plurality of echo signals, wherein each scout image includes a coronal position image, a sagittal image, and an axial image; a phase difference of two of the plurality of scout images is calculated, and phase difference maps of the plurality of slice positions are generated respectively as the phase data of the plurality of slice positions.

In some embodiments, the plurality of echo times (TEs) may be two or more, and embodiments of the present application are not limited thereto. In MR, a difference between at least two of the plurality of echo times TEs is an integer multiple of a period length corresponding to a resonance frequency difference between water and fat. For example, under the condition of 1.5 T, a difference in rotation frequencies of hydrogen protons in water and fat is 220 Hz. Therefore, in order to enable hydrogen protons in the water and fat to be in the same phase at different echo times, the difference between at least two of the plurality of echo times is an integer multiple of 4.5 ms. Two echo times (double echoes, for example, the time difference is an integer multiple of 4.5 ms) are used as an example for illustration.

In some embodiments, two echo signals corresponding to two different echo times are obtained, and for each echo signal, in a K-space, signals with different phase information and frequency information are filled at corresponding positions according to a predetermined data filling manner, and a scout image corresponding to each echo signal is obtained through reconstruction. For a specific method for generating the scout image, reference may be made to the prior art, and will not be repeated herein.

Figure 2:
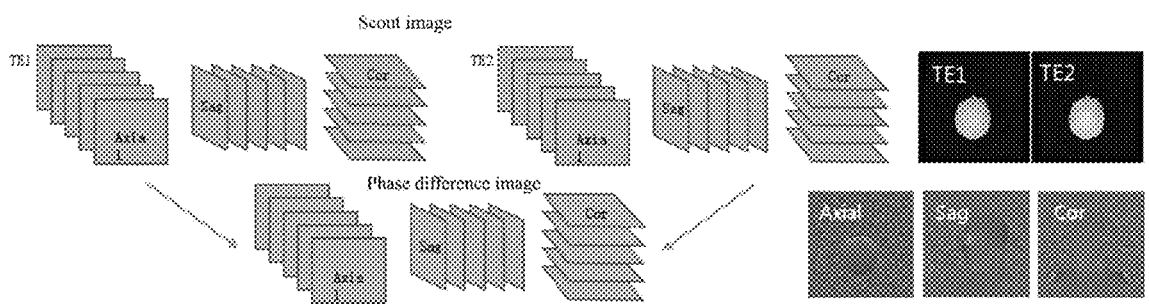
FIG. 2 is a schematic diagram of a scout image and a phase map according to an embodiment of the present application.

In some embodiments, for each slice position, two (groups of) scout images are obtained, and a phase difference between the two scout images is calculated to obtain phase data corresponding to the slice position (hereinafter also referred to as a phase map). FIG. 2 is a schematic diagram of scout images and phase maps of a plurality of (5) slice positions. As shown in FIG. 2, the scout images (on three planes) of the plurality of slice positions are obtained at TE1 and TE2, respectively. For two scout images on the same plane at each slice position, a phase difference is calculated to obtain a phase map corresponding to the slice position on the plane.

In some embodiments, a multi-echo scout scan requires longer repetition time (TR) than a single-echo scout scan. Therefore, in order to reduce scanning time required for the scout scan, in 102, during the scout scan, the number of phase encoding steps may be reduced to obtain low-resolution scout images. Using a double echo scan as an example, during the double echo scout scan, a phase encoding step size may be reduced to half of a phase encoding step size of a single echo scout scan to keep the scanning time of the scout scan unchanged.

In some embodiments, in order to compensate for the loss of resolution caused by the reduction of the phase encoding step size, the method may further include (not shown): inputting the low-resolution scout images into a neural network to obtain high-resolution scout images.

In some embodiments, optionally, amplitude data (hereinafter also referred to as amplitude maps (for example, determined on the basis of amplitude information in echo signals) may be extracted from the low-resolution scout images, and the low-resolution amplitude maps may be input into a neural network to obtain high-resolution scout images.

Figure 3:
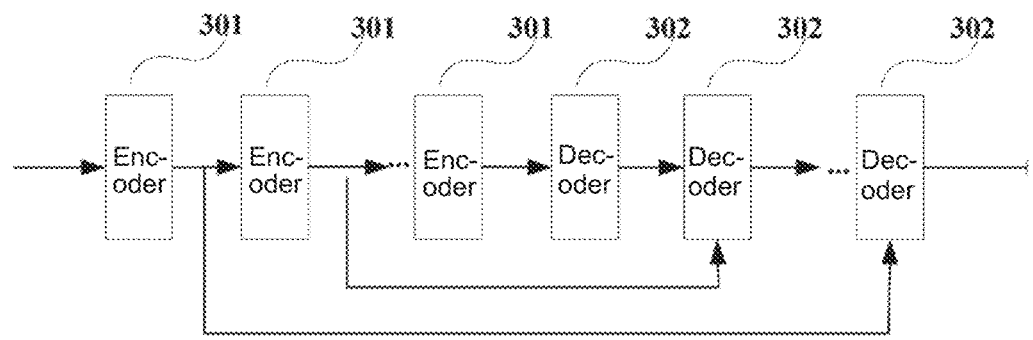
FIG. 3 is a schematic diagram of a neural network structure according to an embodiment of the present application.

In some embodiments, the neural network adopts an encoder-decoder structure. FIG. 3 is a schematic diagram of the structure of the neural network. As shown in FIG. 3, the neural network includes a plurality of encoders 301 connected in sequence and a plurality of decoders 302 connected in sequence, wherein each encoder 301 includes an input layer, a convolution layer, a pooling layer, and an output layer, the input layer of a first encoder is used to receive the low-resolution scout images, and each subsequent encoder is used to receive an output result of a previous encoder to perform convolution, max-pooling, and other processing on the output result. Each decoder 302 is in cascade connection with a symmetrical encoder, for example, the first decoder is cascaded symmetrically with the last encoder, the second decoder is cascaded symmetrically with the penultimate encoder, the third decoder is cascaded symmetrically with the third to last encoder, and so on. The composition of each decoder is similar to that of the encoder, except that each decoder has two input ends, and one input end is used to receive a feature map output by a previous decoder, and the other input end is used to receive a feature map output by an encoder symmetrically cascaded therewith. The decoder is used to stitch the two feature maps together, the deconvolution layer is used to up-sample the stitching processing result, and the output layer is used to output high-resolution scout images. The above neural network in FIG. 3 is only an example for illustration, and the present application is not limited thereto.

In some embodiments, the neural network may use a network model in the prior art. For example, the network model may be U-Net, E-net, etc. The U-net model is used as an example for illustration below.

Figure 4:
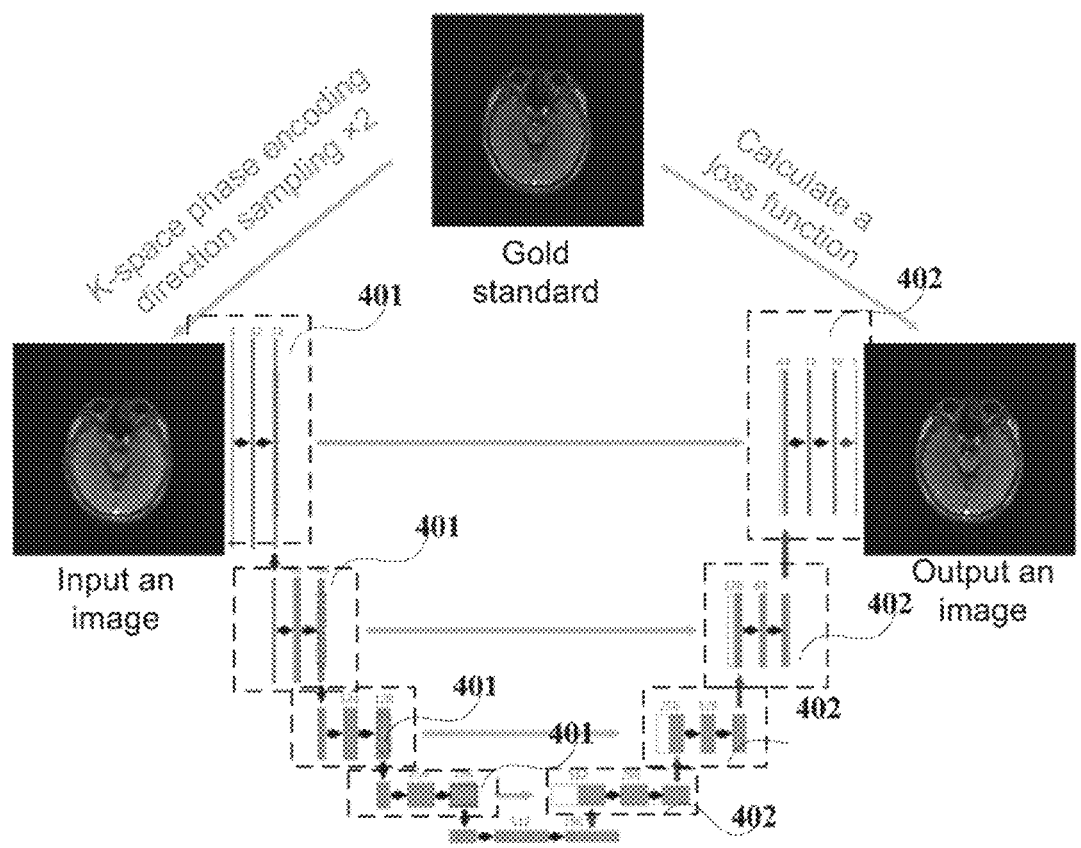
FIG. 4 is a schematic diagram of a U-net model according to an embodiment of the present application.

FIG. 4 is a schematic structural diagram of the U-net model. As shown in FIG. 4, the neural network includes four encoders 401 and four decoders 402. The first encoder is symmetrically cascaded with the last decoder, and the second encoder is symmetrically cascaded with the penultimate decoder, the third encoder is symmetrically cascaded with the third to last decoder, and the fourth encoder is symmetrically cascaded with the fourth to last decoder. The encoder 401 down-samples (maxpooling) an input image, and the decoder 402 up-samples the input image. For example, the down-sampling process of the encoder 401 includes performing two 3*3 convolution operations on the input image, and then performing one 2*2 max-pooling. The number of convolution kernels of the four encoders 401 is doubled in turn. For example, the number of convolution kernels is 32, 64, 128, 256, and 512 in turn. The four encoders 401 are equivalent to four down-sampling operations. The up-sampling process of one decoder 402 includes performing two 3*3 convolutions, taking half of convolution kernels to perform up-sampling (transposed convolution), then copying and cutting a feature map of a corresponding cascaded encoder, and splicing the feature map with a feature map obtained by up-sampling of the previous decoder. The four decoders 402 are equivalent to four up-sampling operations.

In some embodiments, the method may further include: (optionally) training the neural network. For example, the training may be performed on the basis of a known input dataset and a known output dataset (image pairs), by setting the number of neurons in the neural network and optimizing network parameters (including but not limited to weights, biases, etc.) to identify a mathematical relationship between the known input and desired output and characterize a mathematical relationship between an input and an output of each layer, so that a loss function converges, so as to train the aforementioned neural network. The loss function may be a cross-entropy function, but this embodiment of the present application is not limited thereto.

Figure 5:
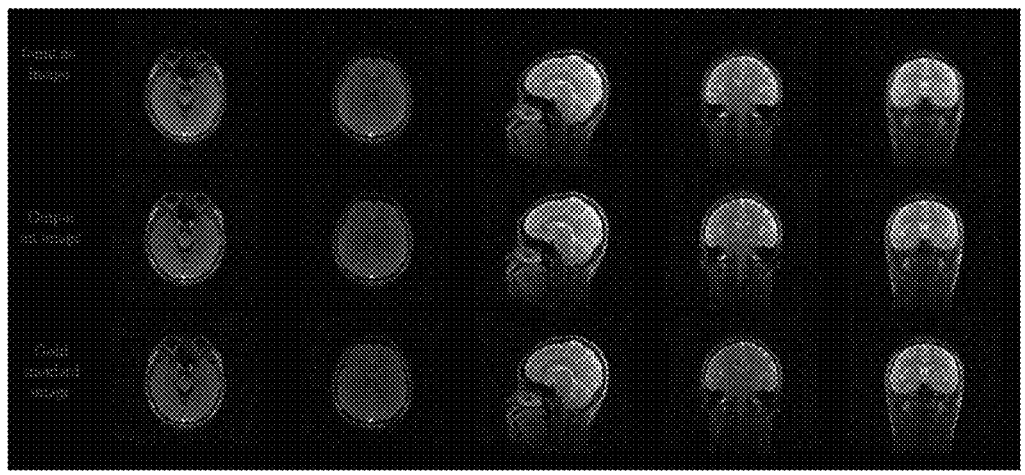
FIG. 5 is a schematic diagram of comparison between a network output result and a gold standard image according to an embodiment of the present application.

In some embodiments, as shown in FIG. 4, the output data set in the aforementioned image pair as the training data set may be full-phase encoded scout images obtained in an actual scan (as a gold standard image, a truth table). The input data set may be half-phase encoding scout images corresponding to the full-phase encoding scout images obtained by calculation (simulation), but this embodiment of the present application is not limited thereto. FIG. 5 is a schematic diagram of comparison between an output result of the neural network and the gold standard image in this embodiment of the present application. As shown in FIG. 5, when an input image is a low-resolution scout image, a high-resolution scout image output by the neural network has a similar effect to that of the gold standard image, and therefore the resolution can be recovered nearly losslessly.

In some embodiments, the high-resolution scout image shows an entire range of an anatomical structure to be imaged, and thus, a region of interest (a region of interest for a formal scan or a FOV for a formal scan) can be determined according to the high-resolution scout image, for example, the region of interest may be determined by means of manual input by an operator or automatic image recognition. For details, reference may be made to the prior art. However, this embodiment of the present application is not limited thereto, and the region of interest may also be directly determined according to the low-resolution scout image, and a determination method is similar to that described above, and will not be repeated herein.

In some embodiments, according to a dynamic range of a B0 distribution and due to influence of a time difference of different echo signals, a phase in a phase map will locally jump by a multiple of $2\pi$, and the phase map will show a non-physical space jump, which in turn leads to an error in calculating a B0 field map. Therefore, in order to more accurately correct non-uniformity of the B0 field, the method may further include: 103, performing phase unwrapping on the phase data of the plurality of slice positions respectively (as shown in FIG. 1).

Moreover, in 104, the three-dimensional space static magnetic field information is determined according to the unwrapped phase data of the plurality of slice positions.

In some embodiments, for a method for the phase unwrapping, reference may be made to the prior art, and this embodiment of the present application is not limited thereto. For example, on a one-dimensional phase vector, if a phase difference between adjacent pixel positions is greater than a threshold, then the value of this phase will be added or subtracted by $2\pi$ to obtain an unwrapped phase, or the unwrapped phase may be determined using a Poisson equation and a least-squares phase solution of the equation in a two-dimensional space, etc., which will not be described herein.

Figure 6:
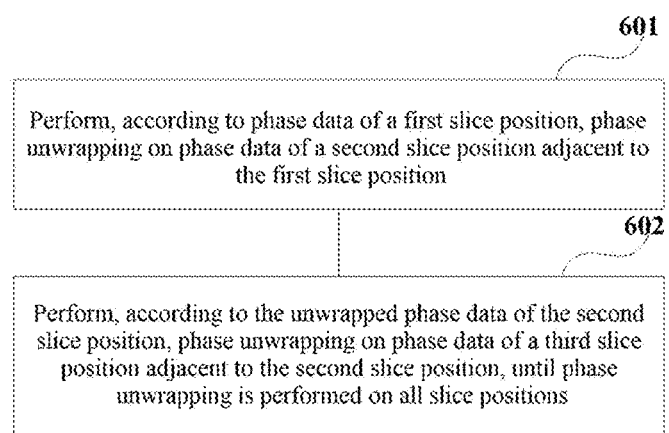
FIG. 6 is a schematic diagram of a phase unwrapping method in 103 according to an embodiment of the present application.

In this embodiment of the present application, as described above, in MR, for example, under the condition of 1.5 T, a difference in rotation frequencies of hydrogen protons in water and fat is 220 Hz. Therefore, in order to enable the hydrogen protons in the water and fat to be in the same phase at different echo times, a difference between at least two of the plurality of echo times $\Delta TE$ is an integer multiple of 4.5 ms. However, the above restriction on differences of a plurality of echo times will limit the dynamic range of the aforementioned phase map. For example, when a difference between two echo times is 4.5 ms, a maximum value of the dynamic range is 220 Hz, and the limited dynamic range (for example, the maximum value can only be up to 220 Hz) will further increase the risk of producing phase wrapping artifacts. Therefore, this embodiment of the present application further proposes a method for phase unwrapping. FIG. 6 shows a schematic diagram of an implementation manner of the operation 103. As shown in FIG. 6, the operation 103 includes:

601, performing, according to phase data of a first slice position, phase unwrapping on phase data of a second slice position adjacent to the first slice position; and 602, performing, according to the unwrapped phase data of the second slice position, phase unwrapping on phase data of a third slice position adjacent to the second slice position, until phase unwrapping is performed on all the slice positions.

Figure 7:
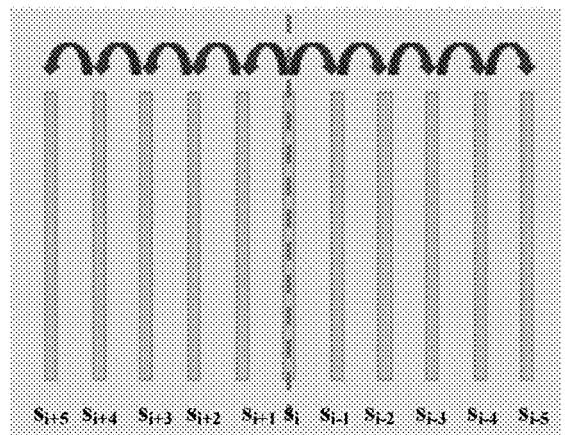
FIG. 7 is a schematic diagram of phase maps of a plurality of slice positions according to an embodiment of the present application.

In some embodiments, the phase data of the plurality of slice positions may be a phase map obtained according to scout images of the plurality of slice positions, and the adjacent slice positions refer to adjacent slices in the plurality of slices, all the slice positions refer to the plurality of slice positions, and the phase data of each slice position may be phase data of the slice position in any orientation in coronal, sagittal, and axial positions, and this embodiment of the present application is not limited thereto. FIG. 7 is a schematic diagram of the phase maps of the plurality of slice positions. As shown in FIG. 7, 11 slice positions are using as an example for illustration. A slice position passing through a magnet center among the plurality of slice positions may be used as the first slice position (hereinafter referred to as $s_i$). There are two second slice positions adjacent to the first slice position, denoted as $s_{i-1}$ and $s_{i+1}$, respectively, a third slice position adjacent to the second slice position $s_{i-1}$ is denoted as $s_{i-2}$, a third slice position adjacent to the second slice position $s_{i+1}$ is denoted as $s_{i+2}$, and so on. The 11 slice positions may be sequentially expressed as: $s_{i+5}$, $s_{i+4}$, $s_{i+3}$, $s_{i+2}$, $s_{i+1}$, $s_i$, $s_{i-1}$, $s_{i-2}$, $s_{i-3}$, $s_{i-4}$, and $s_{i-5}$.

In some embodiments, phase unwrapping may be performed on phase data of $s_{i-1}$ and phase data of $s_{i+1}$ according to phase data of $s_i$, to obtain unwrapped phase data of $s'_{i-1}$ and unwrapped phase data of $s'_{i+1}$; phase data of $s_{i-2}$ and phase data of $s_{i+2}$ may be unwrapped according to the phase data of $s'_{i-1}$ and the phase data of $s'_{i+1}$, to obtain unwrapped phase data of $s'_{i-2}$ and unwrapped phase data of $s'_{i+2}$; phase data of $s_{i-3}$ and phase data of $s_{i+3}$ may be unwrapped according to the phase data of $s'_{i-2}$ and the phase data of $s'_{i+2}$, to obtain unwrapped phase data of $s'_{i-3}$ and unwrapped phase data of $s'_{i+3}$; phase data of $s_{i-4}$ and phase data of $s_{i+4}$ may be unwrapped according to the phase data of $s'_{i-3}$ and the phase data of $s'_{i+3}$, to obtain unwrapped phase data of $s'_{i-4}$ and unwrapped phase data of $s'_{i+4}$; phase data of $s_{i-5}$ and phase data of $s_{i+5}$ may be unwrapped according to the phase data of $s'_{i-4}$ and the phase data of $s'_{i+4}$, to obtain unwrapped phase of $s'_{i-4}$ and unwrapped phase data of $s'_{i+4}$.

The following uses the phase unwrapping of the phase data of $s_{i+1}$ according to the phase data of $s_i$ as an example to illustrate how to perform phase unwrapping on the phase data of the slice position $s_{i+1}$ adjacent to the slice position $s_i$ according to the phase data of the slice position $s_i$. The phase unwrapping operations of the phase data of the other slice positions are the same, and will not be repeated herein.

Figure 8:
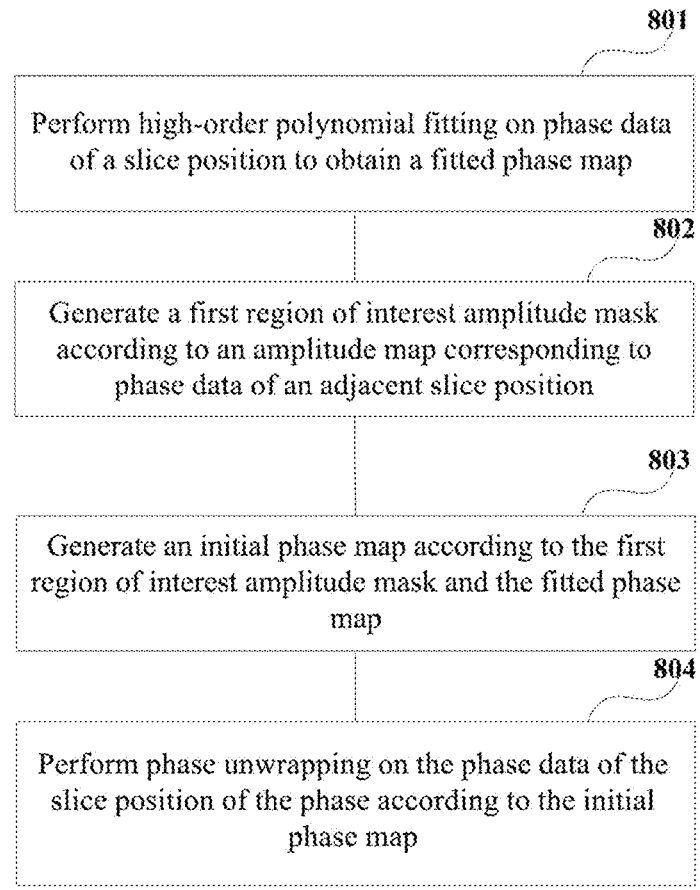
FIG. 8 is a schematic diagram of a method for performing phase unwrapping on phase data of a slice position according to an embodiment of the present application.
Figure 9:
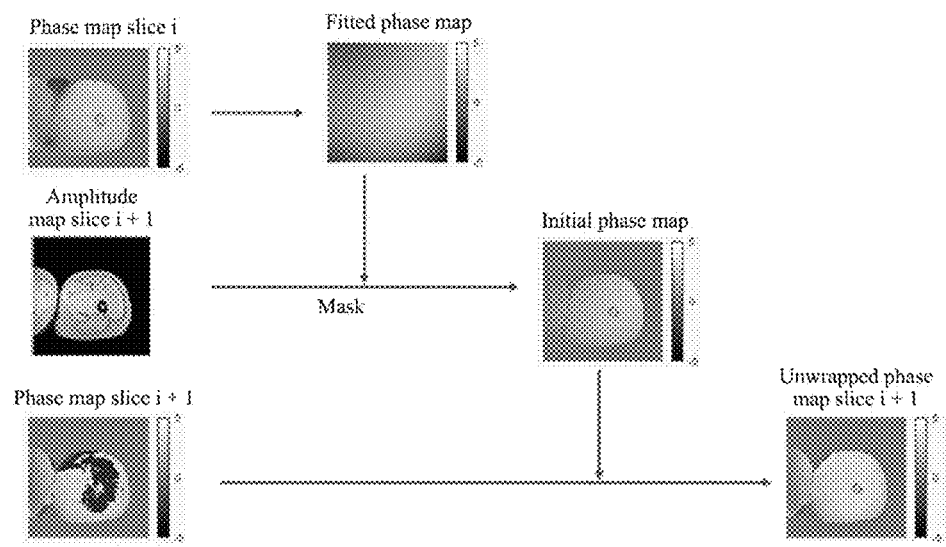
FIG. 9 is a schematic diagram of an implementation manner of performing phase unwrapping on phase data of a slice position according to an embodiment of the present application.
Figure 10:
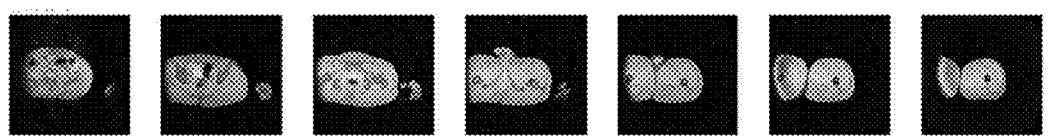
FIG. 10 is an example diagram of a region of interest amplitude map according to an embodiment of the present application.
Figure 11:
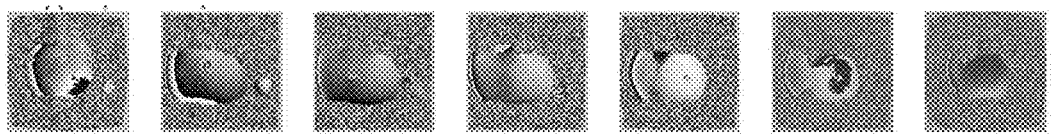
FIG. 11 is an example diagram of a wrapped phase map according to an embodiment of the present application.

FIG. 8 and FIG. 9 are schematic diagrams of an implementation manner of performing, according to phase data of a slice position, phase unwrapping on phase data of a slice position adjacent to the slice position. As shown in FIG. 8, the method includes:

801, performing high-order polynomial fitting on the phase data of the slice position to obtain a fitted phase map;

802, generating a first region of interest amplitude mask according to an amplitude map corresponding to phase data of the adjacent slice position;

803, generating an initial phase map according to the first region of interest amplitude mask and the fitted phase map; and 804, performing phase unwrapping on the phase data of the slice position of the phase according to the initial phase map.

In some embodiments, in 801, high-order polynomial fitting (e.g., third-order polynomial fitting) may be performed on the phase data of the slice position to obtain the fitted phase map. In 802, the amplitude map may be extracted from a scout image of the adjacent slice position as the amplitude map corresponding to the phase data of the adjacent slice position, and the first region of interest amplitude mask MASK1 may be generated according to the amplitude map. For example, in MASK1, a pixel value of a position corresponding to a position with an amplitude within a preset range (for example, a position of an organized structure, and the preset range may be determined as needed) in the amplitude map is set to 1, and pixel values of other positions are set to 0, but this embodiment of the present application is not limited thereto. In 803, the first region of interest amplitude mask is multiplied by the fitted phase map to generate the initial phase map. In 804, phase unwrapping is performed on the phase data of the slice position of the phase according to the initial phase map. For example, as shown in FIG. 9, high-order polynomial fitting (such as third-order polynomial fitting) is performed on the phase data of $s_i$ (phase map slice A), to obtain a fitted phase map; an amplitude map (amplitude map slice i+1) corresponding to the phase data of $s_{i+1}$ is extracted from a scout image of $s_{i+1}$, a first region of interest amplitude mask MASK1 is generated according to the amplitude map, and the MASK1 is multiplied by the fitted phase map to generate an initial phase map; in 804, phase unwrapping is performed on the phase data (phase map slice i+1 of $s_{i+1}$) of the slice position of the phase according to the initial phase map, to obtain an unwrapped phase map slice i+1 of $s'_{i+1}$.

In some embodiments, in 804, first processing is performed on each row or each column of the phase data of the adjacent slice position. The first processing needs to use the initial phase map, that is, use the initial phase map to determine an initial value of a second phase, for example, the initial value of the second phase is equal to a phase corresponding to each position in the initial phase map. The first processing includes: generating an target function according to the first phase and the second phase at each position in a row or a column; determining the value of the second phase when the value of the target function is minimum; and using the value of the second phase as an unwrapped phase.

In some embodiments, the target function $\Psi(\omega)$ may be expressed by the following formula 1):

$$\Psi(\omega) = \sum_j Mag_j[1 - \cos(Phase_j - \omega_j \Delta TE)], \quad \text{Formula 1)}$$

where j represents each pixel position in a row or column in the phase map of the adjacent slice position, $Phase_j$ represents a phase to be unwrapped (first phase) of this position j, $\omega_j \Delta TE$ represents the second phase, and the initial value of the second phase is the phase corresponding to the position j in the initial phase map, and $Mag_j$ represents the amplitude of the position j in the amplitude map corresponding to the phase data of the adjacent slice position. The value of $Mag_j[1-\cos(Phase_j-\omega_j \Delta TE)$ of each position j in a row or column is summed to obtain the target function. Since the phase in the initial phase map is an unwrapped phase, the optimization can be closest to a global minimum. A value $\omega_t$ that makes the target function $\Psi(\omega)$ minimum $\omega_j$ is determined, and the value of the second phase $\omega_t \Delta TE$ is used as the unwrapped phase.

In some embodiments, for the phase data of the adjacent slice position, the above first processing may be performed on each row or each column in units of rows or in units of columns, so as to complete phase unwrapping of the phase data, which is not limited in this embodiment.

Figure 12:
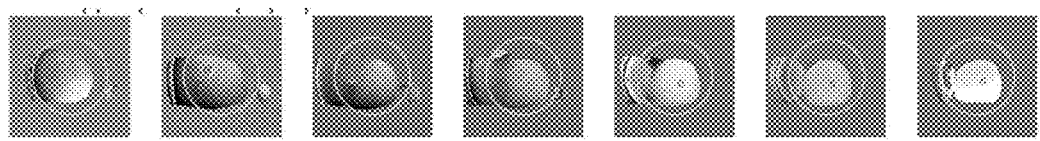
FIG. 12 is an example diagram of an unwrapped phase map according to an embodiment of the present application.
Figure 13:
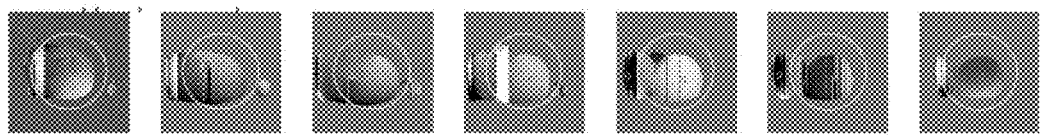
FIG. 13 is an example diagram of an unwrapped phase map obtained by a method from the prior art.

FIG. 10 to FIG. 13 are a series of example diagrams of a region of interest amplitude map, a wrapped phase map, an unwrapped phase map obtained by the method in 801-804, and an unwrapped phase map obtained from a method in the prior art, as shown in FIG. 12 and FIG. 13, in FIG. 12, the image maintains good continuity in a region of interest, while in FIG. 13, the image is discontinuous in a row direction.

Therefore, performing, according to phase data of a slice position, phase unwrapping on phase data of a slice position adjacent to the slice position can minimize influence of chemical shifts, so that a phase map has better continuity and is smoother, and shows good performance especially at cavity and tissue boundaries.

In some embodiments, in 104 and 106, high-order polynomial fitting may be performed according to the phase data of the plurality of slice positions to obtain three-dimensional space static magnetic field information (e.g., 3D B0 volume) corresponding to globally continuous slice positions. That is to say, by means of polynomial fitting, a B0 field distribution of slice positions where a scanning sequence scan is not performed can be obtained. After a region of interest is determined, a slice position in the region of interest is obtained, and a shimming value of the slice position in the region of interest is determined from the globally continuous 3D B0 volume. Optionally, a second region of interest mask may be determined according to the set scanning FOV and anatomical structure, and the second region of interest mask is multiplied by the phase data (phase maps) of the plurality of slice positions, and then high-order polynomial fitting is performed, which is not limited in this embodiment of the present application. A method for determining the second region of interest mask is similar to that of the first region of interest mask, and will not be repeated herein.

In some embodiments, in 104 and 106, in order to reduce the amount of computation, only three-dimensional space static magnetic field information (hereinafter referred to as a sub-B0 volume) corresponding to locally continuous slice positions corresponding to the slice position in the region of interest may be determined. That is, a predetermined number of slice positions that are close to the slice position in the region of interest may be selected from the plurality of slice positions; high-order polynomial fitting is performed on phase data of the predetermined number of slice positions, to obtain the three-dimensional space static magnetic field information corresponding to the locally continuous slice positions; and a shimming value corresponding to the slice position in the region of interest is determined from the three-dimensional space static magnetic field information corresponding to the continuous slice positions. The predetermined number may be preset as a value according to requirements, or may be determined according to a distance between each slice position and the target slice position. For example, if the distance between the slice position and the target slice position is less than or equal to 10 mm or 20 mm, then the slice position belongs to the predetermined number of slice positions. The shimming value includes a shimming value in a first direction and a shimming value in a second direction different from the first direction, the first and second directions being parallel to the slice plane.

Figure 14:
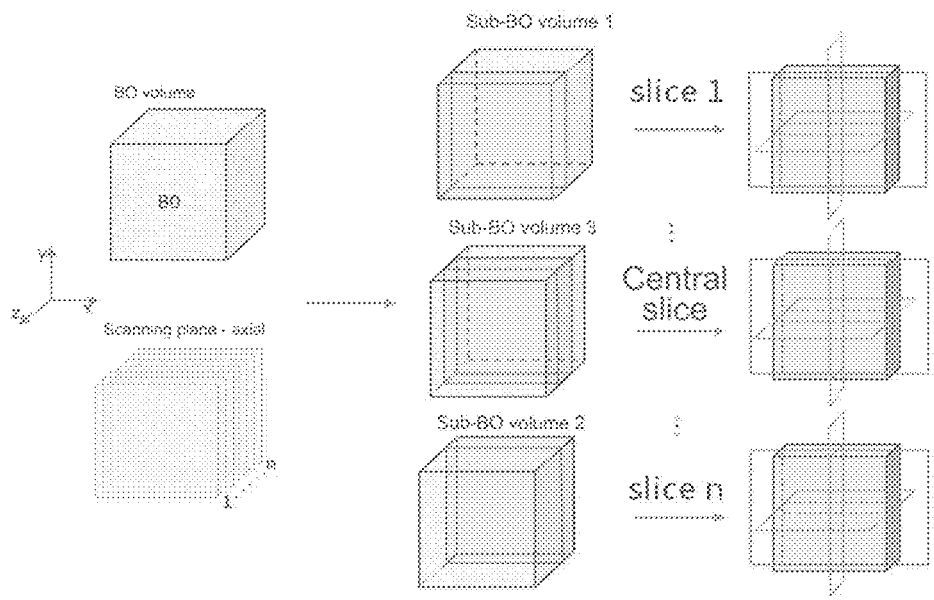
FIG. 14 is a schematic diagram of three-dimensional space static magnetic field information corresponding to locally continuous slice positions.

FIG. 14 is a schematic diagram of the three-dimensional space static magnetic field information corresponding to the locally continuous slice positions. As shown in FIG. 14, slice positions in a Z direction (for example, a scanning plane is an axial position) in the figure are sequentially numbered slice 1, slice 2, . . . , and slice n. When the slice position (target slice) in the region of interest is slice 1, a predetermined number of slice positions close to slice 1 may be selected from the plurality of slice positions, and high-order polynomial fitting is performed on phase data of the predetermined number of slice positions, to obtain a sub-B0 volume 1, and a shimming value (including an X-direction shimming value and a Y-direction shimming value) of slice 1 is determined according to the sub-B0 volume 1; when the slice position (target slice) in the region of interest is slice n, a predetermined number of slice positions close to slice n may be selected from the plurality of slice positions, and high-order polynomial fitting is performed on phase data of the predetermined number of slice positions, to obtain a sub-B0 volume 2, and a shimming value (including an X-direction shimming value and a Y-direction shimming value) of slice n is determined according to the sub-B0 volume 2; when the slice position (target slice) in the region of interest is a central slice, a predetermined number of slice positions close to the central slice may be selected from the plurality of slice positions, high-order polynomial fitting is performed on phase data of the predetermined number of slice positions, to obtain a sub-B0 volume 3, and a shimming value (including an X-direction shimming value and a Y-direction shimming value) of the central slice is determined according to the sub-B0 volume 3.

The above uses one target slice as an example to illustrate how to determine the shimming value. When there are a plurality of target slices, the above processing may be performed on each target slice to determine a shimming value of each target slice, or the above processing may be performed on one target slice first, and after a sub-B0 volume is obtained, shimming values of respective continuous slices in the sub-B0 volume may be determined, the respective continuous slice positions including the aforementioned plurality of target slice positions, and then shimming values of the plurality of target slices may be determined.

In some embodiments, for a method for determining the shimming value according to the B0 field information, reference may be made to the prior art, which is not limited in this embodiment of the present application. For example, an autoshim algorithm may be used to fit first-order derivative images of the phase map in a first direction and a second direction different from the first direction in the B0 field by using a least square method to calculate a first-order component and a constant component, and the first-order components in the first direction and the second direction are used as shimming values, which will not be repeated herein.

In some embodiments, in 106, a central frequency offset of the slice position image in the region of interest may further be calculated according to the three-dimensional space static magnetic field information, and a shimming value in a third direction (as shown in FIG. 14, a Z-direction shimming value) may be calculated according to the central frequency offset. For example, the phase map of the target slice position (B0 field distribution) may be determined according to the B0 volume or the sub-B0 volume. For example, an offset of the phase map of the target slice, i.e., a central frequency offset, is calculated (for example, a constant term in a second-order non-linear fitting result is used as the offset). This offset is used as the shimming value in this third direction.

It should be noted that the above FIG. 1 to FIG. 14 merely schematically illustrate the embodiments of the present application, but the present application is not limited thereto. For example, the order of execution between operations may be suitably adjusted. In addition, some other operations may also be added or some of these operations may be omitted. Those skilled in the art could make appropriate variations according to the above disclosure, rather than being limited by the disclosures of FIG. 1 to FIG. 14.

The above embodiments merely provide illustrative description of the embodiments of the present application. However, the present application is not limited thereto, and appropriate variations may be made on the basis of the above embodiments. For example, each of the above embodiments may be used independently, or one or more of the above embodiments may be combined.

It can be seen from the above embodiments that the shimming value of each slice in the region of interest is determined by using the phase data obtained during the scout scan process, thereby making it possible to reduce the pre-scanning time and more accurately correct non-uniformity of the B0 field, so as to provide better performance in terms of fat saturation in MRI.

Embodiments of Second Aspect

An embodiment of the present application provides an imaging method of a magnetic resonance system. The same content as that of the embodiments of the first aspect is not repeated herein.

Figure 15:
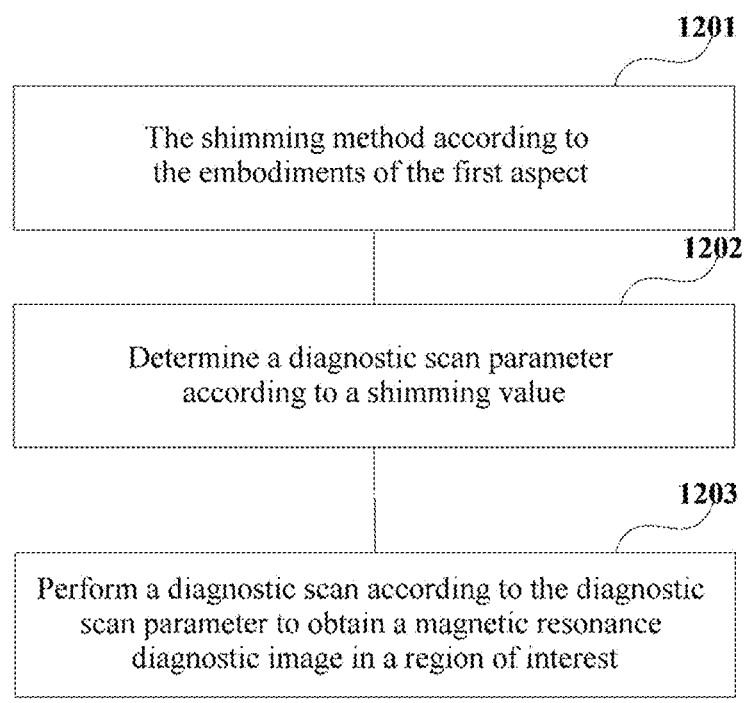
FIG. 15 is a schematic diagram of an imaging method of a magnetic resonance system according to an embodiment of the present application.

FIG. 15 is a schematic diagram of the imaging method of a magnetic resonance system according to an embodiment of the present application. As shown in FIG. 15, the imaging method of the magnetic resonance system includes:
  1201, the shimming method of the embodiments of the first aspect;
  1202, determining a diagnostic scan parameter according to the shimming value; and
  1203, performing a diagnostic scan according to the diagnostic scan parameter to obtain a magnetic resonance diagnostic image in the region of interest.

In some embodiments, in 1202, shimming settings may be performed according to the shimming values in the first direction and the second direction, and central frequency settings may be performed according to the shimming value in the third direction. The diagnostic scan parameter at least includes the shimming settings and the central frequency parameter, and additionally, may further include conventional settings for scan parameters such as a scan range, a scan protocol, and the like. In 1203, when the magnetic resonance system performs the diagnostic scan, the central frequency may be set according to the diagnostic scan parameter, and a shimming control signal may be generated. The shimming control signal is used to control a current of a shimming coil in the magnetic resonance system to generate a compensating magnetic field for a static magnetic field to shim the static magnetic field, which can optimize the uniformity of the static magnetic field, thereby obtaining a magnetic resonance diagnostic image in the region of interest with better performance. For details of the scanning parameter, the diagnostic scan, and how to obtain the magnetic resonance diagnostic image, reference may further be made to embodiments of the third aspect, which will not be repeated herein.

Figure 16:
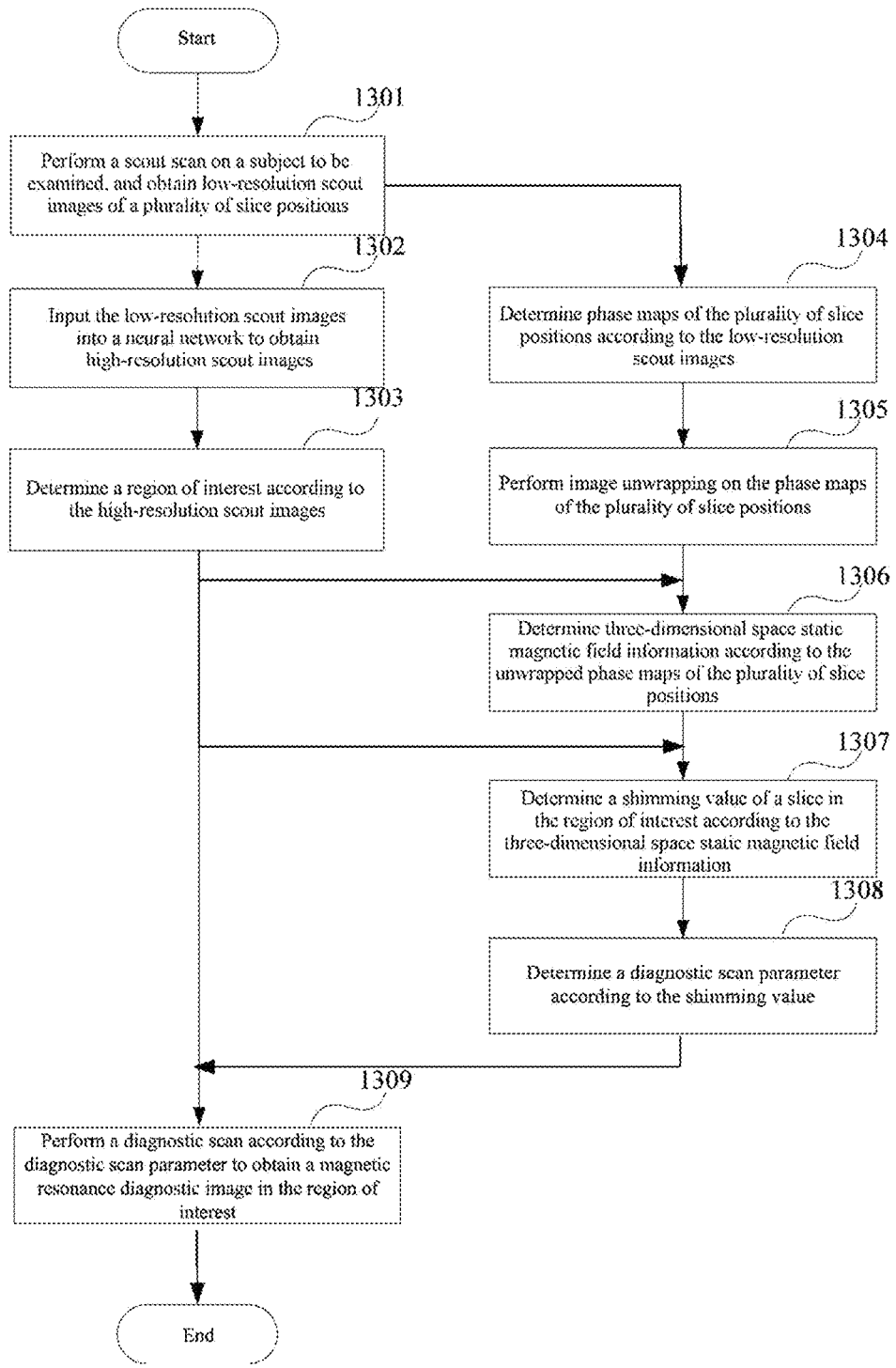
FIG. 16 is a schematic diagram of an imaging method of a magnetic resonance system according to an embodiment of the present application.

FIG. 16 is a schematic diagram of an implementation manner of the imaging method of the magnetic resonance system of the present application. As shown in FIG. 16, the method includes:
  1301, performing a scout scan on a subject to be examined, and obtaining low-resolution scout images of a plurality of slice positions;
  1302, inputting the low-resolution scout images into a neural network to obtain high-resolution scout images;
  1303, determining a region of interest according to the high-resolution scout images;
  1304, determining phase data of the plurality of slice positions according to the low-resolution scout images;
  1305, performing image unwrapping on the phase data of the plurality of slice positions;
  1306, determining three-dimensional space static magnetic field information according to the unwrapped phase data of the plurality of slice positions;
  1307, determining a shimming value of a slice in the region of interest according to the three-dimensional space static magnetic field information.
  1308, determining a diagnostic scan parameter according to the shimming value; and
  1309, performing a diagnostic scan according to the diagnostic scan parameter to obtain a magnetic resonance diagnostic image in the region of interest.

For implementation manners of the above 1301-1307, refer to the embodiments of the first aspect, and for implementation manners of 1308 and 1309, reference may be made to 1202-1203, which will not be repeated herein.

In some embodiments, prior to the scout scan, a pre-scan may be performed. During the pre-scan, pre-setting of the system may be completed. For example, frequency adjustment may be performed to determine the Larmor frequency of proton resonance of the present scan (or a center frequency of the current magnetic resonance examination) on the basis of feedback of magnetic resonance signals at different frequencies, and a radio-frequency emission intensity adjustment may be performed to determine radio-frequency transmission power of the current scan on the basis of feedback of magnetic resonance signals at different radio-frequency transmission intensities. For details, reference may be made to the prior art, which are not numerated herein.

It should be noted that FIG. 15 and FIG. 16 merely schematically illustrate the embodiments of the present application, but the present application is not limited thereto. For example, the order of execution between operations may be suitably adjusted. In addition, some other operations may also be added or some of these operations may be omitted. Those skilled in the art could make appropriate variations according to the above content, rather than being limited by the disclosures of FIG. 15 and FIG. 16.

The above embodiments merely provide illustrative description of the embodiments of the present application. However, the present application is not limited thereto, and appropriate variations may be made on the basis of the above embodiments. For example, each of the above embodiments may be used independently, or one or more of the above embodiments may be combined.

It can be seen from the above embodiments that the shimming value of each slice in the region of interest is determined by using the phase data obtained during the scout scan process, thereby making it possible to reduce the pre-scanning time and more accurately correct non-uniformity of the B0 field, so as to provide better performance in terms of fat saturation in MRI.

Embodiments of Third Aspect

An embodiment of the present application further provides a magnetic resonance imaging system.

Figure 17:
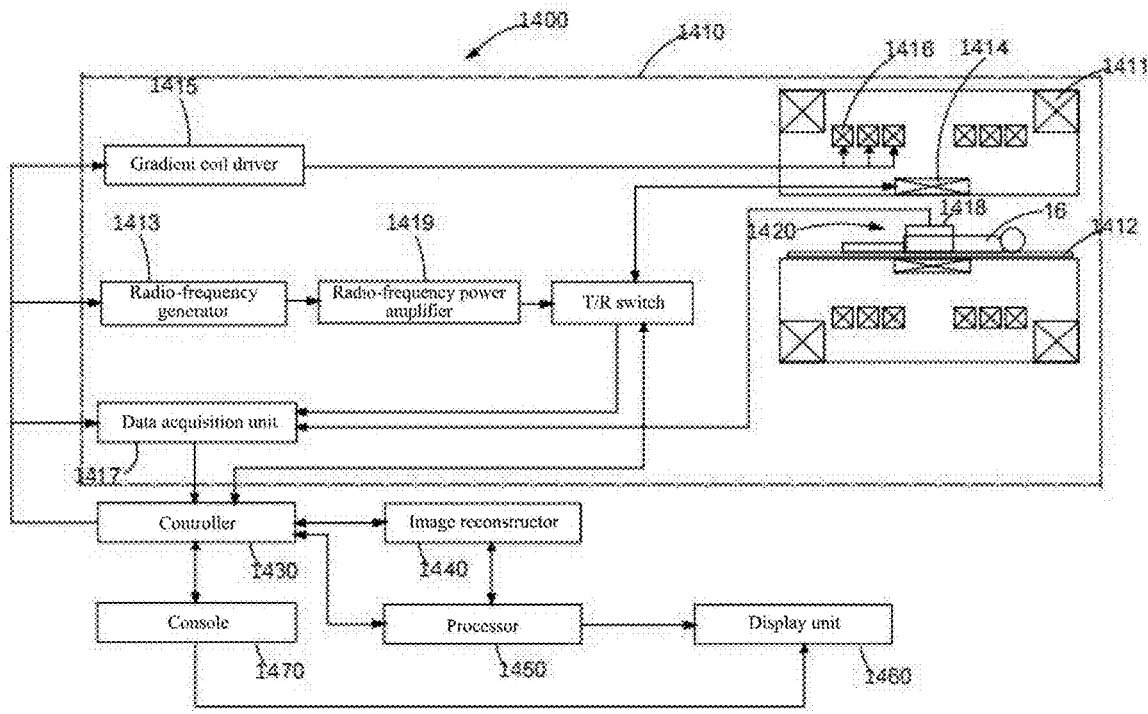
FIG. 17 is a schematic diagram of a magnetic resonance imaging system according to an embodiment of the present application.

FIG. 17 is a schematic compositional diagram of the magnetic resonance imaging system. As shown in FIG. 17, the system 1400 includes: a scanning unit 1410; a controller 1430, which is configured to control the scanning unit to perform a scout scan to obtain phase data of a plurality of slice positions; and a processor 1450, which is configured to determine three-dimensional space static magnetic field information according to the phase data of the plurality of slice positions, and determine a shimming value of a slice in a region of interest according to the three-dimensional space static magnetic field information. The same content as that of the embodiments of the first and second aspects will not be repeated.

In some embodiments, the controller 1430 is further configured to determine a diagnostic scan parameter according to the shimming value, and control the scanning unit 1410 to perform a diagnostic scan according to the diagnostic scan parameter to obtain a magnetic resonance diagnostic image in the region of interest.

In some embodiments, for implementation manners of the controller 1430 and the processor 1450, reference may be made to the embodiments of the first aspect or the second aspect. The functions of the controller 1430 and the processor 1450 may be integrated into one chip, or implemented by separate chips, which is not limited in this embodiment of the present application.

In some embodiments, the controller 1430 in the magnetic resonance imaging system 1400 is coupled to the scanning unit 1410 to control the scanning unit 1410 to perform the aforementioned scout scan or diagnostic scan on a subject (e.g., the human body) 16 to be examined.

In some embodiments, the scanning unit 1410 may include a main magnet assembly 1411, a table 1412, a radio-frequency generator 1413, a radio-frequency power amplifier 1419, a radio-frequency transmitting coil 1414, a surface coil 1418, a gradient coil driver 1415, a gradient coil assembly 1416, and a data acquisition unit 1417.

The main magnet assembly 1411 usually includes an annular superconducting magnet defined in a housing. The annular superconducting magnet is mounted in an annular vacuum container. The annular superconducting magnet and the housing thereof define a cylindrical space surrounding the subject 16, such as a scanning chamber 1420 shown in FIG. 17. The main magnet assembly 1411 generates a static magnetic field (also referred to as a constant magnetic field or a main magnetic field), i.e., a B0 field, in a Z-direction of the scanning chamber 1420. Typically, a uniform portion of the B0 field is formed in a central region of the main magnet.

The table 1412 is configured to carry the subject 16, and travel in the Z direction to enter or exit the aforementioned scanning chamber 1420 in response to the control of the controller 1430. For example, in one embodiment, an imaging volume of the subject 16 may be positioned in a central region of the scanning chamber with uniform magnetic field strength so as to facilitate scanning imaging of the imaging volume of the subject 16. The aforementioned Z direction is typically a direction extending from the head to the feet (or from the feet to the head) when the subject 16 is positioned on the table 1412. For example, a selected layer may be a slice at any position in the Z direction.

The magnetic resonance imaging system 1400 uses the formed B0 field to transmit a static magnetic field to the subject 16 located in the scanning chamber, so that protons in a resonant region in the body of the subject 16 process in an ordered manner to generate a longitudinal magnetization vector.

The radio-frequency generator 1413 is configured to generate a radio-frequency pulse, such as a radio-frequency excitation pulse, in response to a control signal of the controller 1430. The radio-frequency power amplifier 1419 is configured to amplify a low-power radio-frequency signal generated by the radio-frequency generator 1413 to generate a high-power radio-frequency signal that can excite a human tissue. The high-power radio-frequency signal may be input to the radio-frequency transmitting coil 1414 via a radio-frequency transmitting line, so that the radio-frequency transmitting coil 1414 transmits a radio-frequency field B1 orthogonal to the B0 field to the subject 16 to excite atomic nuclei in the aforementioned resonant region to generate a transverse magnetization vector.

The radio-frequency transmitting coil 1414 may include, for example, a body coil disposed along an inner circumference of the main magnet, or a local coil dedicated to local imaging. After the radio-frequency excitation pulse ends, the proton group becomes out-of-phase, the macroscopic transverse magnetization vector in the tissue gradually decays, a free induction decay signal, namely, a magnetic resonance signal that can be acquired, is generated during the process in which the transverse magnetization vector of the object 16 is gradually restored to zero.

The gradient coil driver 1415 is configured to provide a suitable current/power to the gradient coil assembly 116 in response to a gradient pulse control signal or a shimming control signal sent from the controller 1430.

The gradient coil assembly 1416, on one hand, forms a varying magnetic field in an imaging space so as to provide three-dimensional position information for the aforementioned magnetic resonance signal, and on the other hand generates a compensating magnetic field of the B0 field to shim the B0 field.

The gradient coil assembly 1416 may include three gradient coils, which are respectively configured to generate magnetic field gradients inclined to three spatial axes (for example, the X-axis, Y-axis, and Z-axis) perpendicular to each other. More specifically, the gradient coil assembly 1416 applies a magnetic field gradient in the slice selection direction (e.g., Z-direction) to vary the field strength in the region so that the precession frequencies of protons of the imaged tissue at different layers of the region are different, so as to achieve layer selection. Those skilled in the art understand that the layer is any one of a plurality of two-dimensional slices distributed in the Z direction in the three-dimensional imaging volume. When the imaging region is scanned, the radio-frequency transmitting coil 1414 responds to the aforementioned radio-frequency excitation signal, then a layer having a precession frequency corresponding to this radio-frequency excitation signal is excited. The gradient coil assembly 1416 applies a magnetic field gradient in a phase encoding direction (e.g., Y-direction) and a frequency encoding direction (e.g., X-direction), respectively, so that the magnetic resonance signals of the excited layers have different phases and frequencies, thereby achieving phase encoding and frequency encoding.

The aforementioned radio-frequency transmitting coil 1414 may be connected to a transmitting/receiving (T/R)

switch. The transmitting/receiving switch is controlled so that the body coil may be switched between a transmitting mode and a receiving mode. In the receiving mode, the radio-frequency transmitting coil may be configured to receive a magnetic resonance signal from the subject 16.

The surface coil 1418 is usually arranged close to a scan part (region of interest) of the subject 16 (for example, covering or laying on the body surface of the subject 16), and the surface coil 1418 is also configured to receive a magnetic resonance signal from the subject 16.

The data acquisition unit 1417 is configured to acquire the aforementioned magnetic resonance signal (for example, received by the body coil or the surface coil) in response to a data acquisition control signal of the controller 1430. In one embodiment, the data acquisition unit 1417 may include, for example, a radio-frequency preamplifier, a phase detector, and an analog/digital converter, where the radio-frequency preamplifier is configured to amplify the magnetic resonance signal, the phase detector is configured to perform phase detection on the amplified magnetic resonance signal, and the analog/digital converter is configured to convert the phase-detected magnetic resonance signal from an analog signal to a digital signal.

The data acquisition unit 1417 is further configured to respond to a data storage control signal of the controller 1430 to store this digitized magnetic resonance signal (or echo) in a K-space. The K-space is a populated space of raw data of magnetic resonance signals with spatial positioning encoding information. The data acquisition unit 117 fills signals with different phase information and frequency information in the corresponding locations in the K-space according to a predetermined data filling method. In one example, the two-dimensional K-space may include a frequency-encoding line Kx and a phase-encoding line Ky. The data acquisition at each level may contain multiple signal acquisition cycles (or repetition times TR), and each signal acquisition cycle may correspond to one change in the magnetic field gradient (incrementally or decrementally) in the phase-encoding direction (i.e., one signal acquisition is performed for each phase encoding gradient applied), and the magnetic resonance signal acquired in each signal acquisition cycle is filled into a frequency-encoding line Kx. Through multiple signal acquisition cycles, multiple frequency encoding lines having different phase information may be filled, and each acquired magnetic resonance signal has multiple decomposition frequencies.

Those skilled in the art can understand that when imaging scanning is performed on the subject 16, the controller 1430 can use a sequence generator (not shown in the figure) to send sequence control signals to the aforementioned components (for example, the radio-frequency generator 1413, the gradient coil driver 1415, etc.) of the scanner 1410, so that the scanning unit 1410 executes a preset scanning sequence.

Those skilled in the art could understand that the "scanning sequence" refers to a combination of pulses having specific amplitudes, widths, directions, and time sequences and applied when a magnetic resonance imaging scan is performed. The pulses may typically include, for example, a radio-frequency pulse and a gradient pulse. The radio-frequency pulses may include, for example, radio-frequency transmission pulses, radio-frequency refocus pulses, inverse recovery pulses, etc. The gradient pulses may include, for example, the aforementioned gradient pulse used for layer selection, gradient pulse used for phase encoding, gradient pulse used for frequency encoding, etc. Typically, a plurality of scanning sequences can be pre-set in the magnetic resonance system, so that the sequence suitable for clinical detection requirements can be selected. The clinical detection requirements may include, for example, an imaging site, an imaging function, an imaging effect, and the like. For example, in the embodiments of the present application, the scanning sequence may be set as a dual-echo FGRE sequence, but the embodiments of the present application is not limited thereto. For details of the scanning sequence, reference may be made to the embodiments of the first aspect.

Performing a magnetic resonance scan on the subject 16 may include a scout scan (three-plane scan) and a diagnostic scan (a formal scan). One or more scanning sequences may be executed during the scout scan and the formal scan. Wherein, during the scout scan, at least one of a coronal scout image, a sagittal scout image, and an axial scout image of the subject may be acquired, and scan parameters of the formal scan, such as the scan range of the formal scan, are determined on the basis of this scout image. Typically, formal scans are performed on subjects to acquire medical images that may be used for clinical diagnosis.

In a single magnetic resonance examination for one subject 16, the scout image acquired from the scout scan may be a prior-scan image acquired prior to the formal scan. The controller 1430 may further increase/decrease/adjust the scanning sequences in response to different process settings selected by a user on the basis of different clinical applications.

Prior to performing one or more scanning sequences of the scout scan or the formal scan, a pre-scan may be performed. During the pre-scan, pre-setting of the system may be completed. For example, frequency adjustment may be performed to determine the Larmor frequency of proton resonance of the current scan (the center frequency of the present magnetic resonance examination) on the basis of feedback of magnetic resonance signals at different frequencies, and a radio-frequency emission intensity adjustment may be performed to determine radio-frequency transmission power of the present scan on the basis of feedback of magnetic resonance signals at different radio-frequency transmission intensities.

The magnetic resonance imaging system 1400 may include an image reconstructor 1440, which is configured to perform an inverse Fourier transform on data stored in the K-space to reconstruct a three-dimensional image or a series of two-dimensional slice images of the imaging volume of the subject 16. Specifically, the image reconstruction unit 1440 may perform the aforementioned image reconstruction on the basis of communication with the controller 1430.

The processor 1450 of the magnetic resonance imaging system 1400 may further perform any required image post-processing on the aforementioned three-dimensional image or any image in an image sequence. The post-processing may be an improvement or adaptive adjustment made to an image in any aspect of contrast, uniformity, sharpness, brightness, artifacts, etc. In one example, the processor 1450 may include a trained deep learning network, or a unit that communicates with the trained neural network. The processor 1450 may further perform image processing on the basis of communication with the controller 1430.

In one embodiment, the controller 1430, the image reconstructor 1440, and the processor 1450 may separately or collectively include a computer processor and a storage medium. The storage medium records a predetermined data processing program to be executed by the computer processor. For example, the storage medium may store a program used to implement scanning processing, image reconstruction, image processing, etc. For example, the storage medium may store a program used to implement the magnetic resonance imaging method according to the embodiments of the present invention. The storage medium may include, for example, a ROM, a floppy disk, a hard disk, an optical disk, a magneto-optical disk, a CD-ROM, or a non-volatile memory card.

The magnetic resonance imaging system 1400 may include a display unit 160, which may be used to display an operation interface and various data, images, or parameters generated in the image acquisition and processing processes.

The magnetic resonance imaging system 1400 includes an operation console 170, which may include user input devices, such as a keyboard, a mouse, etc. The controller 1430 may communicate with the scanning unit 1410, the image reconstructor 1440, the processor 1450, the display unit 1460, etc., in response to a control command generated by a user on the basis of operating the console 170 or an operation panel/button, etc., disposed on the housing of the main magnet.

It can be seen from the above embodiments that the shimming value of each slice in the region of interest is determined by using the phase data obtained during the scout scan process, thereby making it possible to reduce the pre-scanning time and more accurately correct non-uniformity of the B0 field, so as to provide better performance in terms of fat saturation in MRI.

In MR phase unwrapping methods from the prior art, for example, in a one-dimensional phase vector, if a phase difference between adjacent pixel positions is greater than a threshold, then the value of the phase will be added or subtracted by $2\pi$ to obtain an unwrapped phase, or a Poisson equation and a least-squares phase solution of the equation may be used in a two-dimensional space to determine the unwrapped phase, etc. In MR, for example, under the condition of 1.5 T, a difference in rotation frequencies of hydrogen protons in water and fat is 220 Hz. Therefore, in order to enable the hydrogen protons in the water and fat to be in the same phase at different echo times, a difference between at least two of the plurality of echo times $\Delta TE$ is an integer multiple of 4.5 ms. However, the above restriction on differences of the plurality of echo times will limit the dynamic range of the aforementioned phase map. For example, when a difference between two echo times is 4.5 ms, a maximum dynamic range is 220 Hz, and the limited dynamic range (for example, the maximum value can only be up to 220 Hz) will further increase the risk of producing phase wrapping artifacts. In addition, an unwrapped phase map obtained by the phase unwrapping methods from the prior art will deviate from a real field strength value, and an image is discontinuous in a row direction, and the algorithm does not have good robustness at cavity and tissue boundaries. Therefore, an embodiment of the present application further proposes a method for phase unwrapping.

Embodiments of Fourth Aspect

Figure 18:
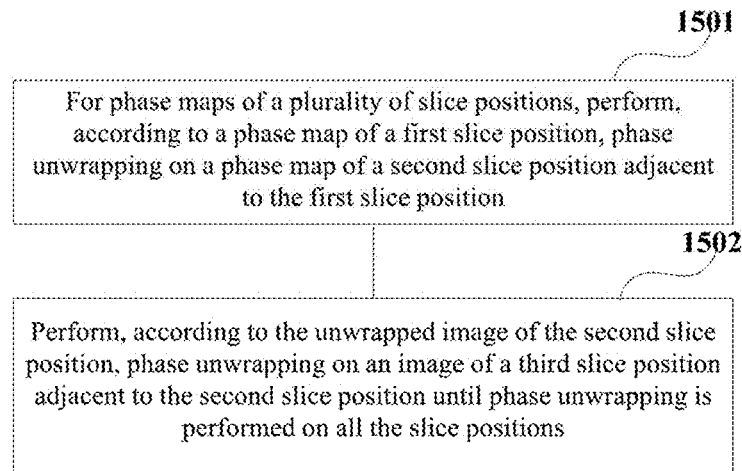
FIG. 18 is a schematic diagram of a phase unwrapping method of a magnetic resonance system according to an embodiment of the present application.

An embodiment of the present application further provides a phase unwrapping method of a magnetic resonance system. The method includes: performing, according to phase data of one slice position, phase unwrapping on phase data of a slice position adjacent to the slice position. FIG. 18 is a schematic diagram of the phase unwrapping method. As shown in FIG. 18, the method includes:

1501, for phase data of a plurality of slice positions, performing, according to phase data of a first slice position, phase unwrapping on phase data of a second slice position adjacent to the first slice position; and

1502, performing, according to the unwrapped phase data of the second slice position, phase unwrapping on phase data of a third slice position adjacent to the second slice position, until phase unwrapping is performed on all the slice positions.

In some embodiments, for implementation manners of 1501-1502, reference may be made to 601-602 and 801-804 of the embodiments of the first aspect, which will not be repeated herein.

Therefore, performing, according to phase data of one slice position, phase unwrapping on phase data of a slice position adjacent to the slice position can minimize influence of chemical shifts, so that a phase map has better continuity and is smoother and shows good performance especially at cavity and tissue boundaries.

Embodiments of Fifth Aspect

Figure 19:
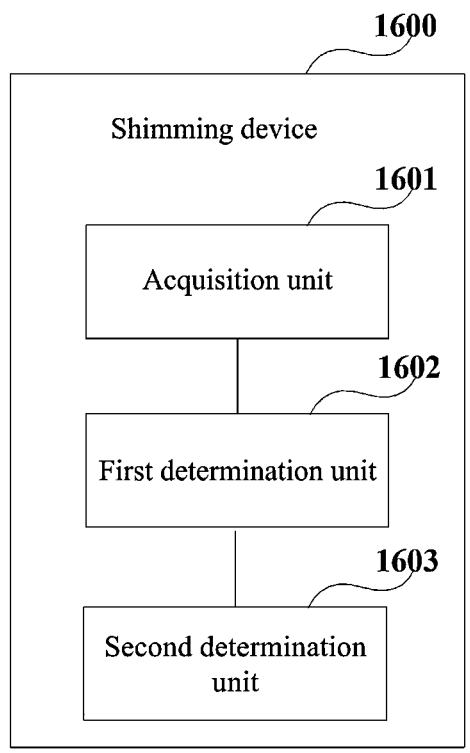
FIG. 19 is a schematic diagram of a shimming device of a magnetic resonance system according to an embodiment of the present application.

An embodiment of the present application further provides a shimming device of a magnetic resonance system. FIG. 19 is a schematic diagram of the shimming device. As shown in FIG. 19, the device 1600 includes:

an acquisition unit 1601, which obtains phase data of a plurality of slice positions after performing a scout scan on a subject to be examined;

a first determination unit 1602, which determines three-dimensional space static magnetic field information according to the phase data of the plurality of slice positions; and a second determination unit 1603, which determines a shimming value of a slice in a region of interest according to the three-dimensional space static magnetic field information.

In some embodiments, for implementation manners of the acquisition unit 1601, the first determination unit 1602, and the second determination unit 1603, reference may be made to the embodiments of the first aspect, which are not repeated herein.

In some embodiments, the functions of the apparatus 1600 may be integrated into a first processor to implement the shimming method described in the embodiments of the first aspect. That is, the first processor may be configured to: obtain phase data of a plurality of slice positions after performing a scout scan on a subject to be examined; determine three-dimensional space static magnetic field information according to the phase data of the plurality of slice positions; and determine a shimming value of a slice in a region of interest according to the static magnetic field information.

Embodiments of Sixth Aspect

Figure 20:
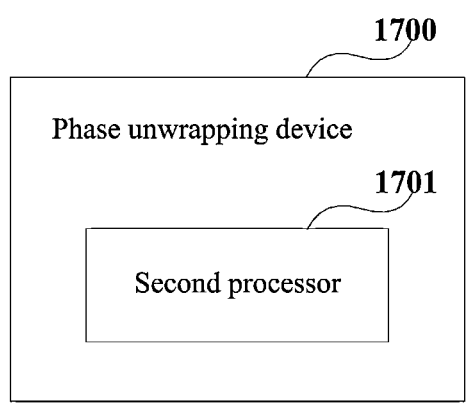
FIG. 20 is a schematic diagram of a phase unwrapping device of a magnetic resonance system according to an embodiment of the present application.

An embodiment of the present application further provides a phase unwrapping device of a magnetic resonance system. FIG. 20 is a schematic diagram of the phase unwrapping device. As shown in FIG. 20, the device 1700 includes: a second processor 1701 configured to perform, according to phase data of one slice position, phase unwrapping on phase data of a slice position adjacent to the slice position. For an implementation manner of the second processor 1701, reference may be made to 601-602 and 801-804 of the embodiments of the first aspect, which will not be repeated herein.

An embodiment of the present application further provides a computer-readable program, where when the program is executed in a shimming device or an MRI system, the program causes a computer to execute the following method in the shimming device or MRI system: obtaining phase data of a plurality of slice positions after performing a scout scan on a subject to be examined; determining three-dimensional space static magnetic field information according to the phase data of the plurality of slice positions; determining a shimming value of a slice in a region of interest according to the three-dimensional space static magnetic field information; or performing, according to phase data of one slice position, phase unwrapping on phase data of a slice position adjacent to the slice position.

An embodiment of the present application further provides a storage medium storing a computer-readable program, where the computer-readable program causes a computer to perform the following method in a shimming device or an MRI system: obtaining phase data of a plurality of slice positions after performing a scout scan on a subject to be examined; determining three-dimensional space static magnetic field information according to the phase data of the plurality of slice positions; determining a shimming value of a slice in a region of interest according to the static magnetic field information; or performing, according to phase data of one slice position, phase unwrapping on phase data of a slice position adjacent to the slice position.

The above device and method of the present application can be implemented by hardware, or can be implemented by hardware in combination with software. The present application relates to such a computer-readable program, when executed by a logical component, causes the logical component to implement the foregoing device or constituent part, or causes the logical component to implement various methods or steps as described above. The present application further relates to a storage medium for storing the above program, such as a hard disk, a magnetic disk, an optical disk, a DVD, a flash memory, etc.

The method/device described with reference to the embodiments of the present application may be directly embodied as hardware, a software module executed by a processor, or a combination of the two. For example, one or more of the functional block diagrams and/or one or more combinations of the functional block diagrams shown in the drawings may correspond to either respective software modules or respective hardware modules of a computer program flow. These software modules may respectively correspond to the steps shown in the figures. These hardware modules can be implemented, for example, by firming the software modules using a field-programmable gate array (FPGA).

The software modules may be located in a RAM, a flash memory, a ROM, an EPROM, an EEPROM, a register, a hard disk, a portable storage disk, a CD-ROM, or any storage medium in other forms known in the art. A storage medium may be coupled to a processor, so that the processor can read information from the storage medium and can write information into the storage medium. Alternatively, the storage medium may be a component of the processor. The processor and the storage medium may be located in an ASIC. The software module may be stored in a memory of a mobile terminal, and may also be stored in a memory card that can be inserted into a mobile terminal. For example, if an apparatus (such as a mobile terminal) uses a large-capacity MEGA-SIM card or a large-capacity flash memory device, the software modules can be stored in the MEGA-SIM card or the large-capacity flash memory device.

One or more of the functional blocks and/or one or more combinations of the functional blocks shown in the accompanying drawings may be implemented as a general-purpose processor, a digital signal processor (DSP), an application specific integrated circuit (ASIC), a field-programmable gate array (FPGA) or other programmable logic devices, discrete gate or transistor logic devices, a discrete hardware assembly, or any appropriate combination thereof for implementing the functions described in the present application. The one or more functional blocks and/or the one or more combinations of the functional blocks shown in the accompanying drawings may also be implemented as a combination of computing apparatuses, such as a combination of a DSP and a microprocessor, multiple microprocessors, one or more microprocessors in communication combination with a DSP, or any other such configuration.

The present application is described above with reference to specific implementations. However, it should be clear to those skilled in the art that such description is merely illustrative and is not intended to limit the scope of protection of the present application. Various variations and modifications could be made by those skilled in the art according to the principle of the present application, and these variations and modifications also fall within the scope of the present application.

The invention claimed is:

1. A method of generating an image of a subject using a magnetic resonance imaging (MRI) system having a processor comprising:
performing a scout scan on the subject to be examined using the MRI system, and obtaining phase data of a plurality of slice positions, wherein the scout scan is used to determine a region of interest for a diagnostic scan;
using the processor to:
determine three-dimensional space static magnetic field information according to the phase data of the plurality of slice positions;
determine a shimming value of a slice in the region of interest according to the three-dimensional space static magnetic field information;
determine a diagnostic scan parameter according to the shimming value;
performing the diagnostic scan of the subject in the region of interest using the MRI system according to the diagnostic scan parameter; and
generating the image of the region of interest.

2. A magnetic resonance system, comprising:
a scanning unit;
a controller, configured to control the scanning unit to perform a scout scan to obtain phase data of a plurality of slice positions, wherein the scout scan is used to determine a region of interest for a diagnostic scan;
a processor, configured to determine three-dimensional space static magnetic field information according to the phase data of the plurality of slice positions and determine a shimming value of a slice in the region of interest according to the three-dimensional space static magnetic field information;
where the processor is further configured to:
determine a diagnostic scan parameter according to the shimming value;
use the scan unit to perform the diagnostic scan of the subject in the region of interest according to the diagnostic scan parameter; and
generate the image of the region of interest.

3. The method according to claim 1, wherein the step of obtaining phase data of a plurality of slice positions comprises:
for each slice position of the plurality of slice positions, obtaining a plurality of echo signals at a plurality of echo times, and generating a plurality of scout images according to the plurality of echo signals, wherein each scout image comprises a coronal image, a sagittal image, and an axial image; and calculating a phase difference between two scout images of the plurality of scout images, and generating phase difference maps of the plurality of slice positions as the phase data of the plurality of slice positions.

4. The method according to claim 3, wherein the scout scan obtains low-resolution scout images by reducing the number of phase encoding steps.

5. The method according to claim 4, further comprising: obtaining high-resolution scout images after inputting the low-resolution scout images into a neural network.

6. The method according to claim 5, further comprising: determining the region of interest according to the high-resolution scout images.

7. The method according to claim 3, wherein a difference between at least two of the plurality of echo times is an integer multiple of a period length corresponding to a difference between resonance frequencies of water and fat.

8. The method according to claim 1, further comprising: performing phase unwrapping on the phase data of the plurality of slice positions respectively; and
determining the three-dimensional space static magnetic field information according to the unwrapped phase data of the plurality of slice positions.

9. An imaging method of a magnetic resonance system, comprising:
the shimming method according to claim 1;
determining a diagnostic scan parameter according to the shimming value; and
performing a diagnostic scan according to the diagnostic scan parameter, and obtaining a magnetic resonance diagnostic image in the region of interest.

10. The method according to claim 8, wherein the step of performing phase unwrapping on the phase data of the plurality of slice positions comprises:
performing, according to phase data of a first slice position, phase unwrapping on phase data of a second slice position adjacent to the first slice position; and
performing, according to the unwrapped phase data of the second slice position, phase unwrapping on phase data of a third slice position adjacent to the second slice position, until phase unwrapping is performed on all the slice positions.

11. The method according to claim 3, further comprising: selecting, from the plurality of slice positions, a predetermined number of slice positions close to the position of the slice in the region of interest,
and the steps of determining three-dimensional space static magnetic field information according to the phase data of the plurality of slice positions, and determining a shimming value of a slice in a region of interest according to the three-dimensional space static magnetic field information comprise:
performing high-order polynomial fitting on phase data of the predetermined number of slice positions, to obtain three-dimensional space static magnetic field information corresponding to locally continuous slice positions; and determining, from the three-dimensional space static magnetic field information corresponding to the locally continuous slice positions, the shimming value corresponding to the slice position in the region of interest.

12. The method according to claim 11, wherein the shimming value comprises a shimming value in a first direction and a shimming value in a second direction different from the first direction.

13. The method according to claim 11, wherein the step of determining the shimming value corresponding to the slice position in the region of interest further comprises:
calculating a central frequency offset of an image of the slice position in the region of interest according to the three-dimensional space static magnetic field information, and calculating a shimming value in a third direction according to the central frequency offset.

14. The method according to claim 10, wherein a slice position passing through a magnet center in the plurality of slice positions is used as the first slice position.

15. The method according to claim 10, wherein the step of performing, according to phase data of one slice position, phase unwrapping on phase data of a slice position adjacent to the slice position comprises:
performing high-order polynomial fitting on the phase data of the slice position to obtain a fitted phase map;
generating a first region of interest amplitude mask according to an amplitude map corresponding to the phase data of the adjacent slice position;
generating an initial phase map according to the first region of interest amplitude mask and the fitted phase map; and
performing phase unwrapping on the phase data of the adjacent slice position according to the initial phase map.

16. The method according to claim 15, wherein the step of performing phase unwrapping on the phase data of the adjacent slice position according to the initial phase map comprises:
performing first processing on each row or each column of the phase data of the adjacent slice position, the first processing comprising:
generating a target function according to a first phase and a second phase at respective positions in a row or a column, wherein initial values of the second phase are equal to phases at the corresponding respective positions in the initial phase map;
determining a value of the second phase when the value of the target function is at a minimum; and
using the value of the second phase as an unwrapped phase.

17. The system according to claim 2, wherein the controller is further configured to determine a diagnostic scan parameter according to the shimming value, and the controller is further configured to control, according to the diagnostic scan parameter, the scanning unit to perform a diagnostic scan to obtain a magnetic resonance diagnostic image in the region of interest.

* * * * *